(12) United States Patent
Roberts et al.

(10) Patent No.: US 8,298,302 B2
(45) Date of Patent: Oct. 30, 2012

(54) FUEL ADDITIVES

(75) Inventors: Martin Roberts, Preston (GB); Christine Ann Blundell, Bickerstaffe (GB); Anthony Finn, Liverpool (GB)

(73) Assignee: Innospec Limited, Cheshire (GB)

( * ) Notice: Subject to any disclaimer, the term of this patent is extended or adjusted under 35 U.S.C. 154(b) by 887 days.

(21) Appl. No.: 11/997,827

(22) PCT Filed: Aug. 1, 2006

(86) PCT No.: PCT/GB2006/002861
§ 371 (c)(1),
(2), (4) Date: Mar. 31, 2008

(87) PCT Pub. No.: WO2007/015080
PCT Pub. Date: Feb. 8, 2007

(65) Prior Publication Data
US 2008/0236030 A1 Oct. 2, 2008

(30) Foreign Application Priority Data
Aug. 3, 2005 (GB) .................................. 0515998.3

(51) Int. Cl.
*C10L 1/19* (2006.01)
(52) U.S. Cl. ........................................... 44/389; 44/398
(58) Field of Classification Search .................... 44/389, 44/398
See application file for complete search history.

(56) References Cited

U.S. PATENT DOCUMENTS

| | | | | |
|---|---|---|---|---|
| 2,993,773 | A | * | 7/1961 | Stromberg ...................... 60/209 |
| 4,448,586 | A | | 5/1984 | Weidig |
| 6,293,977 | B1 | | 9/2001 | Caprotti et al. |

FOREIGN PATENT DOCUMENTS

| | | |
|---|---|---|
| EP | 0277735 A2 | 8/1988 |
| GB | 2363798 A | 1/2002 |
| JP | 01306691 | 12/1989 |
| JP | 05125014 | 5/1993 |
| JP | 2003292589 | 10/2003 |
| WO | WO 94/17160 | 8/1994 |
| WO | WO 97/45507 | * 12/1997 |

OTHER PUBLICATIONS

The Russian Version and an English Translation of Extract from the Russian Standard TY 2411-05766801-97, Alpha-Olefins, Fraction C16-C18. A product of thermo catalytic oligomerization of ethylene. Used in the manufacture of alkylsalicylate additives and fatty acides. TY 2411-067-05766801-97.
Notification of Reasons for Refusal, mailing date Mar. 27, 2012 (Heisei 24), patent application No. 2008-524584, date of preparation Mar. 24, 2012, Articles applied: Article 29(1), Article 29(2), Article 36.

* cited by examiner

*Primary Examiner* — Ellen McAvoy
*Assistant Examiner* — Latosha Hines
(74) *Attorney, Agent, or Firm* — Burns & Levison, LLP; Janine M. Susan

(57) ABSTRACT

The invention provides a fuel additive compound represented by the general formula (I)

$$HO-R^2-O-\underset{R^1}{\underset{|}{C}}(=O)-\underset{O}{\overset{R^3}{C}}H-O-R^2-\left[O-\underset{R^1}{\underset{|}{C}}H-\underset{O}{\overset{}{C}}(=O)-O-R^2\right]_n-OH$$

wherein n is zero or an integer from 1 to 20 and in each succinic acid moiety one of $R^1$ and $R^3$ is a $C_3$-$C_{80}$ internal olefin moiety, and the other of $R^1$ and $R^3$ is hydrogen. Additive compositions containing such compounds have low viscosity and are useful in increasing the lubricity of middle distillate fuels.

10 Claims, No Drawings

FUEL ADDITIVES

This invention relates to fuel additives, more particularly to additives which increase the lubricity of the fuel.

Environmental concerns have recently initiated new legislative requirements to reduce the sulfur content of diesel fuels. The processes employed to reduce sulfur levels to meet these new requirements also remove naturally-occurring lubricity agents in diesel fuel and so limit the fuel's ability to lubricate and protect the various parts of the engine's fuel injection system from wear.

It is known that esters of fatty acids are effective additives which will improve the lubricity of low sulfur fuels. For example WO94/17160 discloses these. Increased lubricity results in lower wear of the surface, as measured, for example by the well known wear scar test described in more detail hereinafter.

WO 97/45507 discloses bis-esters of alkenyl succinic acids with ethylene glycol, propylene glycol, glycerol and polyoxyalkylenes. The succinic acids have 10-32 carbon atoms in the alkenyl chain.

We have now discovered a class of esterified alkenyl succinic acids that have significantly improved performance as lubricity additives over the esters disclosed in WO97/45507. In addition they may have lower viscosity, which allows formulation benefits and even the possibility, in some cases, that a carrier or solvent may not be needed.

In accordance with a first aspect of the present invention there is provided a fuel additive compound represented by the general formula (I)

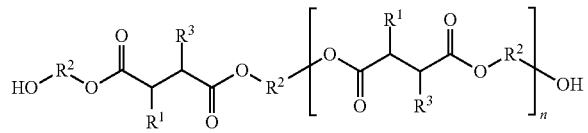

wherein n is zero or an integer from 1 to 20 and in each succinic acid moiety one of $R^1$ and $R^3$ is a $C_3$-$C_{80}$ internal olefin moiety, and the other of $R^1$ and $R^3$ is hydrogen.

Thus in any individual succinic acid moiety, if $R^1$ is alkenyl then $R_3$ is hydrogen and vice versa. However the pattern of substitution along the oligomer chain need not be identical.

The fuel additive compounds may be used alone or as a mixture of one or more esters or in combination with any other lubricating compound or any other additive which provides a lubricity effect.

The fuel additive compounds have the advantage of lower viscosity compared to the esters disclosed in WO97/45507

Preferably n is an integer from 1 upwards, more preferably from 2 upwards. Preferably n is an integer up to 11, more preferably up to 10, more preferably up to 8, more preferably up to 6 and most preferably up to 5.

Preferably one of $R^1$ and $R^3$ is a $C_{12}$-$C_{80}$ group or $C_{12}$-$C_{32}$ group, for example or $C_{15}$-$C_{18}$ group, especially a $C_{16}$ group.

Compounds containing $R^1$ and $R^3$ groups formed from internal olefins possess an advantageously low viscosity, such that a carrier or solvent is often not required.

It is not necessary for $R^1$ or $R^3$ to be exclusively a single chain length nor completely linear, i.e. there can be some branching such as methyl, ethyl and higher alkyl branching. $R^1$ and $R^3$ can be derived from polymerized ethylene, propylene, butylenes, etc.

An internal olefin as used herein means any olefin containing predominantly a non-alpha double bond, that is a beta or higher olefin. Preferably such materials are substantially completely beta or higher olefins, for example containing less than 10% by weight alpha olefin, more preferably less than 5% by weight or less than 2% by weight. Typical internal olefins include Neodene 1518IO available from Shell.

Internal olefins are sometimes known as isomerised olefins and can be prepared from alpha olefins by a process of isomerisation known in the art, or are available from other sources. The fact that they are also known as internal olefins reflects that they do not necessarily have to be prepared by isomerisation.

The molecular weight of the alkenyl group $R^1$ or $R^3$ is preferably at least 42, preferably at least 140, preferably at least 168, most preferably at least 180. The molecular weight of the alkenyl group $R^1$ or $R^3$ is preferably up to 1200, more preferably up to 1120, most preferably up to 448.

$R^2$ in formula (I) is a linking group, and preferably is the residue of a polyhydroxy alcohol, preferably a compound of formula $HO(CH_2CH_2)_xOH$, $HO(CH_2CHCH_3)_xOH$, $HO(CH_2CH_2O)_xH$, $HO(CH_2CHCH_3O)_xH$, or $HO(CH_2CHOHCH_2)_xOH$ with x=1-10. The value of x in these compounds is most preferably 1 or 2. Highly preferred are dihydroxy alcohols, preferably having primary hydroxyl groups, at the respective ends of the carbon backbone. In particular $R^2$ can be ethylene glycol.

In accordance with a second aspect of the present invention there is provided a fuel additive composition comprising compounds of general formula I as defined above. Typically the composition comprises a range of compounds of formula I as defined above, of different degrees of oligomerisation. Indeed, one might expect the monomer species (n is zero) to be typically present as well; together with, perhaps, some compounds in which n is higher than is defined herein. Thus compositions are not excluded in which in some compounds present n is a higher number than is defined herein. That is to say, the process by which compounds of the present invention may be made (which process will hereinafter be described and defined) is one which may produce a range of compounds of different molecular weights (but which either consist of or include ones defined by the formula given above).

In accordance with a third aspect of the present invention there is provided a fuel dosed with a compound of the first aspect, or with a composition of the second aspect.

The compounds of formula (I) may be added to middle distillate fuels of poor lubricity, such as those with poor inherent lubricity, and those which have been exposed to hydrotreatment or desulfurisation processes thereby lowering the sulfur concentration to 0.5% w/w or less, e.g. 0.2% w/w, 0.05% w/w or lower, for example diesel fuels (typical distillation range 150-400° C.), marine fuels (typical distillation temperature above 250° C.) and heating oils (typical distillation range 150-450° C.), and also to gasolines (typical distillation range 30-210° C.), kerosines (typical distillation range 140-300° C.) and heavy fuel oils (typical distillation range 300-600° C.). A further aspect of the invention thus comprises methods of increasing the lubricity of such fuels by addition of the compounds of the invention.

Compounds of formula (I) may be dosed in amounts between 5 and 5000 ppm, preferably between 10 and 500 ppm and most preferably between 30 and 300 ppm, to improve the lubricity properties of the fuels.

Diesel fuels and heating oils will typically contain less than 0.2% w/w sulfur and may contain, in addition to the additive compositions of this invention, any of the other additives commonly added as minor components, such as cetane improvers, cold flow improvers, detergent/dispersant additives, antifoam additives, dehazing additives, combustion improvers, antioxidants, corrosion inhibitors, etc.

As used herein, "gasoline" refers to motor fuels, for example meeting ASTM standard D-439 and/or EN228, and includes blends of distillate hydrocarbon fuels with oxygenated components, such as MTBE, ETBE, ethanol, etc. as well as the distillate fuels themselves. The fuels may be leaded or unleaded, and may contain, in addition to the additive compositions of this invention, any of the other additives conventionally added to gasolines, such as scavengers, anti-icing additives, octane requirement improvers, detergent packages, antioxidants, demulsifiers, corrosion inhibitors, etc.

The invention also provides fuel additive compositions suitable for use in any of the previous aspects of the invention, the compositions comprising one or more compounds of formula (I), where necessary in a fuel-miscible solvent, for example a hydrocarbon solvent. Examples of suitable solvents include an aromatic 100 solvent, an aromatic 150 solvent, toluene, xylene, Shellsol (available from Shell), and furthermore optionally containing other ingredients conventionally used in fuel additive packages.

The compounds of formula (I) may for example be prepared by reacting an anhydride of general formula II

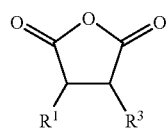

with a polyhydroxy alcohol which yields a residue $R^2$ as defined above, such reaction being carried out essentially to completion as measured by acid value.

The starting anhydride of general formula II is conveniently prepared by addition of an olefin across the double bond of maleic anhydride by processes known per se.

In accordance with a fourth aspect of the present invention there is provided a process for the preparation of a compound of the general formula I, which process comprises reacting an anhydride of formula II as defined above with a polyhydroxy alcohol. Suitably the compound of formula II has been prepared by reaction of an internal olefin with maleic anhydride. Preferably the ene reaction to produce the compound of formula II takes place at an elevated temperature, for example 160-240° C. for an extended period, for example 4-6 hours. Preferably unreacted maleic anhydride is removed, for example by vacuum distillation. This is preferably done at the end of the reaction period. The product of this reaction may be used without further work-up, in the second step.

The second step, the reaction of a compound of formula II with a polyhydroxy alcohol preferably takes place at an elevated temperature, for example 160-240° C., for an extended period, for example 12-48 hours. Preferably water is removed as the reaction proceeds. Preferably unreacted polyhydroxyl alcohol is removed, for example by vacuum distillation, at the end of the reaction period. The product may be used without further work-up.

In accordance with a fifth aspect of the present invention there is provided the use of an additive comprising a compound of the first aspect or of a composition of the second aspect, in the treatment of a fuel in order to achieve a lubricity improvement, compared with the corresponding untreated base fuel. A further benefit is that the additive may have reduced viscosity, compared with corresponding esters having a corresponding alpha-olefinic group $R^1$ or $R^3$.

The invention is illustrated by the following examples.

Preparation of Compounds

A. Maleic anhydride (288.5 g) was added to Neodene 1518 isomerised olefin (882.5 g) at 200° C. The reaction mixture was heated at 210° C. for several hours then residual maleic anhydride was removed by distillation under vacuum. Some of the product from this reaction (372.9 g) was then mixed with ethylene glycol (338 g) and the mixture heated to 200° C. for 24 hours, water formed as a by-product of the reaction was continuously removed. Following removal of excess ethylene glycol by vacuum distillation, the reaction mixture was cooled to room temperature and the resulting liquid was used directly, or in a solvent, as a fuel additive.

B. Chevron C16 isomerised olefin (850 g) and maleic anhydride (289.9 g) were mixed at 200° C. and then heated at 210-215° C. for 10 hours, unreacted maleic anhydride was removed after this time by distillation under vacuum. Some of the product from this reaction (284.3 g) was then mixed with ethylene glycol (238.2 g) and the mixture heated to 200° C. for 22 hours, water formed as a by-product of the reaction was continuously removed. Following removal of excess ethylene glycol by vacuum distillation, the reaction mixture was cooled to room temperature and the resulting liquid used directly, or in a solvent, as a fuel additive.

Comparative Example

C. Polyisobutylene (Indopol L6, 622.2 g) and maleic anhydride (164.26 g) were mixed at 200° C. and then heated at 205° C. for 10 hours, residual maleic anhydride was then removed by distillation under vacuum. Some of the product from this reaction (352.6 g) was then mixed with ethylene glycol (226.5 g) and heated to 200° C. for 22 hours, water formed as a by-product of the reaction was continuously removed. Following removal of excess ethylene glycol by vacuum distillation, the viscous product can be used directly as a fuel additive or diluted in a solvent such as a hydrocarbon solvent.

Analysis

Samples prepared following the experimental methods as described above were analysed for viscosity prior to dilution. Significantly lower viscosities were found for compounds derived from internal olefins as exemplified by Additives A and B, than for comparative example, typical of esters as disclosed in WO 97/45507.

|  | Viscosity @40° C. |
|---|---|
| Additive A | 640 mPas |
| Additive B | 595 mPas |
| Additive C | 19200 mPas |

Improvement of Fuel Lubricity

A High Frequency Reciprocating Rig (HFRR) bench test, such as described in SAE Technical Paper 932692, can measure the lubricity of base fuel and fuel dosed with lubricity additives. The results of such a test are reported as ball wear in terms of mean wear scar diameter. Lower wear scar diameters are indicative of better lubricity. HFRR wear scar diameter results are compared below for a typical North American middle distillate fuel which has been treated with the compounds A and B of formula (I), and a comparative compound C. The fuel contains less than 0.05% w/w sulfur content.

| Additive | Active treat rate (mg/l) | Wear Scar |
|---|---|---|
| Base Fuel | 0 | 705 |
| Additive A | 86 | 386 |
| Additive B | 86 | 454 |
| Additive C | 86 | 595 |

The invention claimed is:

1. A method of improving the lubricity of a fuel comprising adding a compound of general formula I to the fuel in order to obtain a lubricity improvement, compared with the corresponding untreated base fuel wherein said compound comprises

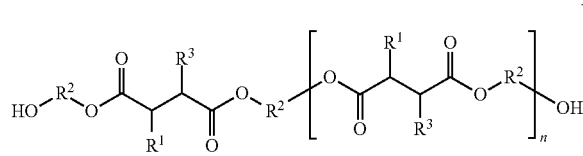

I wherein n is zero or an integer from 1 to 20 and in each succinic acid moiety one of $R^1$ and $R^3$ is a $C_3$-$C_{80}$ internal olefin moiety, and the other of $R^1$ and $R^3$ is hydrogen, and $R^2$ is the residue of a polyhydroxy alcohol.

2. A method of improving the lubricity of a fuel comprising adding a composition to the fuel in order to obtain a lubricity improvement, compared with the corresponding untreated base fuel, wherein said composition comprises compounds of general formula I:

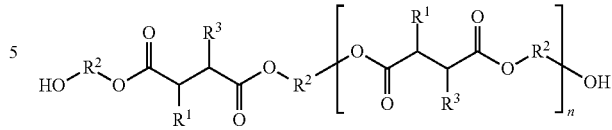

I wherein n is zero or an integer from 1 to 20 and in each succinic acid moiety one of $R^1$ and $R^3$ is a $C_3$-$C_{80}$ internal olefin moiety, and the other of $R^1$ and $R^3$ is hydrogen, and $R^2$ is the residue of a polyhydroxy alcohol.

3. The method as claimed in claim 1, wherein n is an integer from 0 to 5.

4. The method as claimed in claim 1, wherein one of $R^1$ or $R^3$ is a $C_{12-32}$ group.

5. The method as claimed in claim 4, wherein one of $R^1$ or $R^3$ is a $C_{15-18}$ group.

6. The method as claimed in claim 2 wherein the compounds of formula I present comprise compounds in which n is an integer from 1 to 11.

7. The method as claimed in claim 6, wherein the fuel is a hydrotreated or desulfurised middle distillate fuel having a sulfur concentration of 0.5% w/w or less.

8. The method as claimed in claim 3, wherein one of $R^1$ or $R^3$ is a $C_{12-32}$ group.

9. The method as claimed in claim 8, wherein one of $R^1$ or $R^3$ is a $C_{15-18}$ group.

10. The method as claimed in claim 1, wherein the fuel is a hydrotreated or desulfurised middle distillate fuel having a sulfur concentration of 0.5% w/w or less.

* * * * *